US006541447B1

(12) United States Patent
Dawson

(10) Patent No.: US 6,541,447 B1
(45) Date of Patent: Apr. 1, 2003

(54) WOUND HEALING COMPOSITION AND METHOD FOR USE THEREOF

(75) Inventor: Monica E. Dawson, Lenexa, KS (US)

(73) Assignee: B & M Healthcare Technologies, Inc., Lenexa, KS (US)

( * ) Notice: Subject to any disclaimer, the term of this patent is extended or adjusted under 35 U.S.C. 154(b) by 0 days.

(21) Appl. No.: 09/388,225

(22) Filed: Sep. 1, 1999

(51) Int. Cl.[7] .................. A61K 38/00; A61K 38/24; A61K 38/27; C07K 14/00
(52) U.S. Cl. ................. 514/2; 514/12; 530/350; 530/399; 530/388.24; 435/69.4; 424/400; 424/581
(58) Field of Search ................. 530/350, 399, 530/388.24; 514/2, 12; 435/69.4; 424/400, 581

(56) References Cited

U.S. PATENT DOCUMENTS

| | | |
|---|---|---|
| 115,032 A | 5/1871 | Crossman |
| 122,621 A | 1/1872 | Masters |
| 240,150 A | 4/1881 | Lawrence et al. |
| 247,818 A | 10/1881 | Gilman |
| 451,307 A | 4/1891 | Miles |
| 2,555,731 A | 6/1951 | Cooper |
| 3,194,732 A | 7/1965 | Neuhauser |
| 3,558,771 A | 1/1971 | Balassa |
| 3,624,201 A | 11/1971 | Balassa |
| 4,219,544 A | 8/1980 | Burg |
| 4,533,635 A | 8/1985 | Guedon et al. |
| 4,604,234 A | 8/1986 | Fujii et al. |
| 4,670,257 A | 6/1987 | Guedon et al. |
| 4,719,111 A | 1/1988 | Wilson |
| 4,808,402 A | 2/1989 | Leibovich et al. |
| 4,832,946 A | 5/1989 | Green |
| 4,839,164 A | 6/1989 | Smith |
| 4,843,063 A | 6/1989 | Seyedin et al. |
| 4,929,442 A | 5/1990 | Powell |
| 4,959,353 A | 9/1990 | Brown et al. |
| 5,023,090 A | 6/1991 | Levin |
| 5,064,655 A | 11/1991 | Uster et al. |
| 5,104,977 A | 4/1992 | Sporn et al. |
| 5,130,298 A | 7/1992 | Cini et al. |
| 5,219,998 A | 6/1993 | Levin et al. |
| 5,460,832 A | 10/1995 | Yamaguchi et al. |
| 5,618,544 A | 4/1997 | Brown |
| 5,637,318 A | 6/1997 | Gross et al. |
| 5,676,975 A | 10/1997 | Dezes et al. |
| 5,849,273 A * | 12/1998 | Bonda et al. .................. 424/59 |

FOREIGN PATENT DOCUMENTS

| | | | |
|---|---|---|---|
| EP | 0338459 A2 * | 10/1989 | ............ A61K/7/06 |
| EP | 0444638 | 9/1991 | |
| FR | 2654342 | 5/1991 | |
| WO | 9118999 | 12/1991 | |

OTHER PUBLICATIONS

Gasior–Chrzan, B., Przeglad Dermatologiczny 75(6) 431–434 (1988) "Wplyw lizozymu bialka jaja kurzego na gojenis standaryzowanych ran skory swnek morskich (Effect of ovalbumin lyzozyme on healing of standard skin wounds in guinea pigs)".*

Katz, M. H., et al, J.Am. Acad. Dermatol., "Human Wound Fluid From Acute Wounds Stimulates Fibroblast and Endothelia Cell Growth", 25:1054–1058 (Dec. 1988).

Stanley, A. C. et al, J. Vasc. Surg., "Reduced Growth of Dermal Fibroblasts From Chronic Venous Ulcers Can Be Stimulated With Growth Factors", 26(6) 994–999 (Dec. 1997).

Lynch, S. E., et al, Proc. Nat'l Acad. Sci. USA, "Role of Platelet–derived Growth Factor in Wound Healing: Synergistic Effects With Other Growth Factors", 84(21): 7696–7700 (Nov. 1987).

Steed, "The Role of Growth Factors in Wound Healing", *Surgical Clinics of North America*, vol. 77, No. 3, pp. 575–586 (Jun. 1997).

Martin, et al., "Growth Factors and Cutaneous Wound Repair", *Progress in Growth Factor Research*, vol. 4, No. 1, pp. 25–44 (1992).

Hom, et al., "Angiogenic Growth Factors: Their Effects and Potential in Soft Tissue Wound Healing", *Ann. Otol. Rhinal. Laryngol.*, vol. 101, No. 4, pp. 349–354 (Apr. 1992).

Katz, "Human Wound Fluid From Acute Wounds Stimulates Fibroblast and Endothelial Cell Growth", *Journal of the American Academy of Dermatology*, vol. 25, No. 6 (Part 1), pp. 1054–1058 (Dec. 1991).

Stanley, et al., "Reduced Growth of Dermal Fibroblasts from Chronic Venous Ulcers Can Be Stimulated with Growth Factors", *Journal of Vascular Surgery*, vol. 26, No. 6, pp. 994–1001 (Dec. 1997).

Lynch, et al, "Role of Platelet–Derived Growth Factor in Wound Healing: Synergistic Effects With Other Growth Factors", *Proc. National Academy of Sciences USA*, vol. 84, No. 21, pp. 7696–7700 (Nov. 1987).

Schultz, et al., "EGF and TGF–Alpha in Wound Healing and Repair", *Journal of Cellular Biochemistry*, vol. 45, No. 4, pp. 346–352 (Apr. 1991).

(List continued on next page.)

Primary Examiner—Karen Cochrane Carlson
Assistant Examiner—Chih-Min Kam
(74) *Attorney, Agent, or Firm*—Mayer, Brown, Rowe & Maw; Joseph A. Mahoney; Thomas R. Stiebel

(57) ABSTRACT

A composition for wound healing and hair growth is disclosed. The composition comprises at least 5.0% by weight of ovalbumin, about 1.0% phenoxyethanol, about 0.5% carbomer, and about 0.3% triethanolamine. The composition may be in the form of a cream, powder, lotion, gel, emulsion, or ointment. Its method for use in wound healing and for hair growth is also disclosed.

20 Claims, No Drawings

OTHER PUBLICATIONS

Flamme, et al., "Overexpression of Vascular Endothelial Growth Factor in the Avian Embryo Induces Hypervascularization and Increased Vascular Permeability Without Alterations of Embryonic Pattern Information", *Developmental Biology*, vol. 171, No. 2, pp. 399–414 (Oct. 1995).

"Pasteurization Keeps Eggs Bacteria–Free", *USA Today*, vol. 124, No. 2611, p. 11 (Apr. 1996).

Fremont, et al., "Crystal Structure of an H–2K (super b)–Ovalbumin Peptide Complex Reveals the Interplay of Primary and Secondary Anchor Positions in the Major Histocompatibility Complex Binding Groove", *Proceedings of the National Academy of Sciences of the United States*, vol. 92, No. 7, pp. 2479–2483, (Mar. 28, 1995).

Niedermann, et al., "The Proteolytic Fragments Generated by Vertebrate Proteasomes: Structural Relationships to Major Histocompatibility Complex Class I Binding Peptides", *Proceedings of the National Academy of Sciences of the United States*, vol. 93, No. 16, pp. 8572–8577, (Aug. 6, 1996).

Qui, et al., "Spatiotemporal Expression Patterns of Chicken Ovalbumin Upstream Promoter–Transcription Factors in the Developing Mouse Central Nervous System: Evidence for a Role In Segmental Patterning of the Diencephalon", *Proceedings of the National Academy of Sciences of the United States*, vol. 91, No. 10, p. 4451–4455, (May 10, 1994).

Kawamoto, et al., "Transforming Growth Factor Type β Stimulates Epidermal Growth Factor–Dependent Cell Growth in vivo and in vitro Senescent Human Skin Fibroblasts", *Cell Structure and Function*, vol. 13, No. 6 (1524) (Dec. 1988).

Satoh, et al., "Charcterization of Endothelial Cell Growth Factor from Serum–Free Culture Supernatant of Human Diploid Fibroblast Cells", *Cell Structure and Function*, vol. 13, No. 6 (1536) (Dec. 1988).

Brown, et al., "Acceleration of Tensile Strength of Incisions Treated with EGF and TGF–β", *Ann. Surg.*, vol. 208, No. 6, pp. 788–794 (Dec. 1988).

Brown, et al., "Stimulation of Healing of Chronic Wounds by Epidermal Growth Factor", *Plastic and Reconstructive Surgery*, vol. 88, No. 2, pp. 189–194 (Aug. 1991).

Brown, et al., "Enhancement of Wound Healing by Topical Treatment with Epidermal Growth Factor", *The New England Journal of Medicine*, vol. 321, No. 2, pp. 76–79 (Jul. 13, 1989).

Chua, et al., "Receptor for Epidermal Growth Factor Retains Normal Structure and Function in Aging Cells", *Mechanisms of Ageing and Development*, vol. 34, pp. 35–55 (1986).

Hollenberg, et al., "Receptors For Insulin and Epidermal Growth Factor–Urogastrone In Adult Human Fibroblasts Do Not Change with Donor Age", *Mechanisms of Ageing and Development*, vol. 11, pp. 37–43 (1979).

Allen, "Cosmetics—Chemical Technology or Biotechnology?", *International Journal of Cosmetic Science*, vol. 6, No. 2 (Apr. 1984).

Sprugel, et al., "The Effects of Different Growth Factors In Subcutaneous Wound Chambers", *Growth Factors and Other Aspects of Wound Healing: Biological and Clinical Implications*, pp. 77–91 (1988).

Knighton, et al., "Amputation Prevention in an Independently Reviewed At–Risk Diabetic Population Using a Comprehensive Would Care Protocol", *The American Journal of Surgery*, vol. 160, pp. 466–472 (Nov. 1990).

Van Brunt, et al., "Growth Factors Speed Wound Healing", *Biotechnology*, vol. 6, pp. 25–30 (Jan. 1988).

Hosgood, "Wound Healing. The Role of Platelet–Derived Growth Factor and Transforming Growth Factor Beta", *Veterinary Surgery*, vol. 22, No. 6, pp. 490–495 (Nov.–Dec. 1993).

Bennett, et al., "Growth Factors and Wound Healing: Biochemical Properties of Growth Factors and Their Receptors", *American Journal of Surgery*, vol. 165, No. 6, pp. 728–737 (Jun. 1993).

Eisinger, et al., "Growth Regulation of Skin Cells by Epidermal Cell–Derived Factors: Implications for Wound Healing", *Proc. National Academy of Science USA*, vol. 85, No. 6, pp. 1937–1941 (Mar. 1988).

Falanga, "Growth Factors and Chronic Wounds: The Need to Understand the Microenvironment", *The Journal of Dermatology*, vol. 19, No. 11, pp. 667–672 (Nov. 1992).

Hudson–Goodman, et al., "Wound Repair and the Potential Use of Growth Factors", *Heart& Lung.*, vol. 19, No. 4, pp. 379–384 (Jul. 1990).

Greenhalgh, "The Role of Growth Factors in Wound Healing", *The Journal of Trauma: Injury, Infection, and Critical Care*, vol. 41, No. 1, pp. 159–167 (Jul. 1996).

Hom, "Growth Factors in Wound Healing", *Otolaryngologic Clinics of North America*, vol. 28, No. 5, pp. 933–953 (Oct. 1995).

Kingsnorth, et al., "Peptide Growth Factors and Wound Healing", *British Journal of Surgery*, vol. 78, No. 11, pp. 1286–1290 (Nov. 1991).

Moulin, "Growth Factors in Skin Wound Healing", *European Journal of Cell Biology*, vol. 68, No. 1, pp. 1–7 (Sep. 1995).

Otau, et al., "Cosmetics Containing Urogastone/Epidermal Growth Factor", *Chemical Abstracts—Essential Oils, Cosmetics*, vol. 104, #192928u, p. 417 (1986).

Ogawa, et al., "Skin Conditioners Containing Epidermal Growth Factor", *Chemical Abstracts—Essential Oils, Cosmetics*, vol. 106, #182467v, p. 395 (1987).

Nonokawa, et al., "Cosmetics Containing Urogastrone", *Chemical Abstracts—Essential Oils, Cosmetics*, vol. 104, #174376h, p. 369 (1986).

Nishiyama, et al., "Skin Cosmetics Containing Saikosaponin b1 and/or b2 and Cell Growth Factors", *Chemical Abstracts—Essential Oils, Cosmetics*, vol. 116, #241736p, p. 407 (1992).

Matauo, et al., "Preparation of Polypeptides for Cosmetics and Pharmaceuticals", *Chemical Abstracts—Essential Oils, Cosmetics*, vol. 117, #219741k, p. 495 (1192).

Kadowaki, et al., "Development of New Host for Gene Recombination and Possibility of Application to Cosmetic Products", *Chemical Abstracts*, vol. 115, #176096t, p. 232 (1991).

"Testimonials From Polygen™ Users", www.polygencare.com/testimonials (Dec. 2001).

* cited by examiner

WOUND HEALING COMPOSITION AND METHOD FOR USE THEREOF

FIELD OF THE INVENTION

This invention pertains to wound healing compositions and, particularly, to such a composition comprising of a growth hormone and growth factor in a balanced mixture that will deliver the maximum therapeutic results with non-healing wounds, burns, trauma, and certain dermatological disorders.

BACKGROUND OF THE INVENTION

1. Overview of the Invention

There have been recent dramatic strides with the discovery of growth factors as wound healing agents. Indeed, the discovery of growth factors has triggered great optimism into the possibility of mastering the art of wound healing and intense effort has been launched on the part of medical researchers and pharmaceutical companies to procure, characterize, and harvest these healing enhancement agents. Because it is believed that administering growth factors to patients with dermal and subdermal wounds enhances the speed by which wounds heal, as discussed in greater detail below, it is the object of this invention to provide a topical composition containing growth factors to increase the body's wound healing properties.

2. Background and Prior Art

Since their discovery almost 30 years ago, growth factors have been shown to stimulate neovascularization in vitro and in animal studies. In the past 10 years, knowledge of growth factors has grown immensely. Broadly defined, growth factors are multifunctional, locally acting, intercellular signaling polypeptides which, among other things, organize and coordinate cellular proliferation. Most growth factors are large peptides or glycoproteins secreted by many cells as a base function, or in response to a challenge, such as a wound or carcinogen. These peptides represent a system of signals that mediate physiologic and pathologic cellular growth and repair, including embryogenesis, wound healing and carcinogenesis.

Currently, there are two known classes of intercellular signaling proteins: (i) endocrine proteins which are long range signaling proteins released into the circulation or other body fluids, and (ii) paracrine proteins which are short range signaling proteins that act locally within tissues. Growth factors are generally considered as paracrine proteins since they are predominantly short range locally acting, intercellular signaling proteins.

There exist six known varieties of growth factors: platelet-derived growth factor (PDGF), epidermal growth factor (EGF), fibroblast growth factor (FGF), insulin-like growth factor (IGF), transforming growth factor beta (TGFβ), and TGFβ Superfamily. In addition to their local mode of action, the different varieties of growth factors share common biological properties. For example, growth factor action is mediated by association with specific, high affinity receptors expressed by the target cells, and growth factors are able to exert their biological effect at low concentrations ($10^{-9}$ to $10^{-11}$M).

Furthermore, on the cellular level, growth factors bind with ligands on the cell surface to generate an intracellular signal on the inside of the cell to modify cellular behavior. Growth factors function by binding to specific cell-surface receptors that are composed of three distinct regions or domains: an extracellular domain, which binds to the growth factor ligand; a transmembrane domain; and an intracellular domain. When the ligand binds to neighboring receptors, conformational changes occur that are transmitted to the intracellular domain and elicit a series of cytoplasmic changes leading to the initiation of the nucleic acid transcription. In many cases, these intracytoplasmic events are enacted through an enzyme, tyrosine kinase, that phosphorylates cytoplasmic proteins, some of which remain in the cytoplasm and some pass to the nucleus with a corresponding gene activation.

Studies have shown that fluid factors isolated from chronic wounds lack the presence of growth factors. Moreover, in vitro studies have shown that growth factors added to wound fluid extracted from postoperative or traumatic wounds have accelerated the wound healing cascade. These facts strongly suggest the important role of growth factors.

One in vitro study examined the effect of human wound fluid on the growth of human dermal fibroblasts and umbilical vein endothelial cells. Katz M H et al., J. Am. Acad. Dermatol., *Human Wound Fluid from Acute Wounds Stimulates Fibroblast and Endothelial Cell Growth*, 25:1054–1058 (December 1988). Katz et al. collected wound fluid from six patients undergoing split-thickness skin and wound fluid from postoperative patients. After seeding the wound fluid in optimal growth media (control) on day 0, cultures of human dermal fibroblasts and umbilical vein endothelial cells were supplemented with or without acute wound fluid on days 1 and 3. The study found that 2% acute wound fluid stimulated the growth of human dermal fibroblasts and umbilical vein endothelial cells when these cells were cultured in 2% fetal bovine serum and endothelial growth medium, respectively. Wound fluid from the postoperative patients caused the same level of stimulation. Furthermore, when anti-platelet-derived growth factor antibody was added to wound fluid, there was a 45% mean reduction in the stimulatory effect on fibroblast growth. This result further suggests that platelet-derived growth factor contributes to the fibroblast growth effect.

It has also been suggested that ulcer healing may be improved by the exogenous provision of specific growth factors. Research has shown that fibroblasts isolated from wound sites on patients proliferated at a slower rate and are morphologically distinct (larger and polyglonal in shape) from normal fibroblasts cells. Stanley A C et al., J. Vasc. Surg., *Reduced Growth of Dermal Fibroblasts from Chronic Venous Ulcers can be Stimulated with Growth Factors*, 26(6):994–999 (December 1997). It was also found that the decreased growth of wound fibroblasts were stimulated by growth factors FGF, EGF, IL-1.

A combination of growth factors produce a magnified effect in stimulating protein synthesis and decreasing protein degradation. They have also been shown to have additive effect in improving whole-body and muscle kinetics. For example, it has been shown that the addition of pure PDGF to a wound site involving the epidermis and dermis has little effect on the morphology or biochemistry of wound healing. Lynch S E et al., Proc. Nat'l. Acad. Sci. USA, *Role of Platelet-Derived Growth Factor in Wound Healing: Synergistic Effects with Other Growth Factors*, 84(21):7696–7700 (November 1987). In contrast, the addition of partially purified PDGF results in significant dose-dependent increases in the width of the newly synthesized connective tissue and epidermal layers. Further, the addition of partially purified PDGF results in significant increases in the rate of protein and DNA synthesis and the total content of these components in biopsies taken from the wound site. Similar effects were obtained when IGF was added in combination with pure PDGF. Combining the growth factors caused a 2.4 fold increase in the width of newly formed connective tissue layer and a 95% increase in epidermal thickness compared with controls. Id. On the other hand, IGF applied alone did not cause similar morphological changes, thus indicating that the synergistic actions of other factors with PDGF are important in the modulation of the wound healing process. Therefore, a combination of growth factors and growth hormones have a potential amplified effect on accelerated non-healing of ulcers, open wound, osteomyelitis, skeletal muscle injuries such as sports and trauma, and burns and dermatological disorders.

Animal and clinical trials using growth factor therapy have produced outstanding results. Healing of a variety of wounds in animals and patients was enhanced by treatment with EGF or TGF-alpha. Several different studies of topically applied growth factors have shown to accelerate healing by stimulating granulation tissue formation and enhancing epithelialization. Epidermal regeneration of partial thickness burns on pigs or dermatome wounds on patients was accelerated with topical application of EGF TGF-alpha, and EGF treatment accelerated healing of gastroduodenal ulcers. Schultz G. et al., J. Cell. Biochem., *EGF and TGF-Alpha in Wound Healing and Repair*, 45(4):346-352 (April 1991). EGF also increased tensile strength of skin incisions in rats and corneal incisions in rabbits, cats, and primates. Id.

Specific use of particular factors is becoming an accepted mode of therapy for many patients with non-healing wounds. Accordingly, there is ample scientific and clinical evidence suggesting that the biological actions of growth factors regulate cell division, differentiation, migrations and gene expression.

The present invention is a composition comprising a mixture of growth factors and growth hormones in a dermatologically safe vehicle, such as a liquid, gel or cream. It is therefore an object of the present invention to provide a wound-healing composition comprising a protein growth factor to treat healing resistant wounds, dialetic ulcers, bedsores, burns, osteomyelitis, trauma wounds, subcutaneous trauma and various forms of dermatitis. The composition is also useful in reducing the formation of scar tissue.

SUMMARY OF THE INVENTION

In accordance with the present invention, it has now been discovered that wounds may be effectively treated with the growth factors that are contained in egg whites of hens. Specifically, topically administered growth factors in pharmacologically effective amounts are useful for increasing the local activity of the body's wound healing process. Accordingly, the present invention is a low cost, over-the-counter, composition containing growth factors isolated from a naturally occurring source—egg whites. The composition may be used to treat any disease state where growth factors play a role including diabetic ulcers, nonhealing wounds, burns, osteomyelitis, trauma wounds, subcutaneous trauma and various forms of dermatitis.

In particular, the wound healing composition is comprised of phenoxyethanol, carbomer, protein and triethanolamine. The protein is ovalbumin from egg whites, which includes a combination growth factors including epidermal growth factor (EGF), transforming growth factor alpha (TGF-Alpha), fibroblast growth factor (acidic) (FGF-a), fibroblast growth factor (basic) (FGF-b).

In a preferred embodiment of the invention, the wound-healing composition comprises about 1.0% by weight of phenoxyethanol, about 0.5% carbomer, about 20% ovalbumin and about 0.3% triethanolamine. These compounds are blended to produce a eutectic mixture in gel, lotion, cream or ointment form. The inventive composition can also be in powder form as well.

It is therefore an object of the present invention to treat mammalian nonhealing wounds manifested by diabetes, burns, trauma and subcutaneous trauma, osteomyelitis, various surgical procedures, and various forms of dermatitis.

It is another object of the present invention to treat wounds with a topical agent that is easily administered, economical and well-tolerated by patients.

It is another object of this invention to provide a composition to stimulate fibroblast production for tissue repair.

It is yet another object of this invention to provide a composition for the stimulation of hair follicle growth.

It is still another object of the present invention to provide a composition for treating non healing wounds by the addition of an individual or combination of growth factors including IGF, PDGF, FGF, EGF, TGFβ and TGFβ Superfamily.

These and other features and advantages of the present invention will be found in the following description of the preferred embodiments and in the claims.

DESCRIPTION OF THE PREFERRED EMBODIMENT

Before the present composition for wound healing is disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

As described above, the present invention is directed to a composition for stimulating cell growth and the healing of wounds by administering a pharmacologically effective amount of growth factors directly to the affected tissue. The composition may be used to treat any type of nonhealing wound whereby fibroblast activity is reduced or ineffective. Such wounds include diabetic non-healing wounds, burns, osteomyelitis, trauma wounds, subcutaneous trauma and various forms of dermatitis. The composition may also be employed to stimulate hair growth on the scalp and other body areas.

The growth factors of the present invention have been identified in hen's egg whites. Ovalbumin is the major constituent of egg whites from the hen comprising about 75% by weight of the egg white. The molecular weight of ovalbumin is approximately 4,500, and ovalbumin is produced under hormonal control by the bird oviduct. It may be isolated and crystallized readily from the filtrate of an acidified mixture of egg white and an equal volume of saturated ammonium sulfate. Sorensen et al., C. R. Trav. Lab. Carlsberg 12, 12 (1917). Alternative methods of isolation of ovalbumin are disclosed by Kekwick et al., Bio-Chem Journal 30: 227 (1930). Ovalbumin can also be separated by electrophoresis and chromatography from about 10 other minor components found in egg whites including avidin (qv), lysozyme (qv), conalbumin (qv), and ovomucoid.

The structure of ovalbumin is that of a complex protein consisting of a single polypeptide chain of about 460 residues (about half of which are hydrophobic), a maximum of 2 phosphate residues per mole, and a oligosaccharide side chain composed of only mannose and glucosamine residues. See Narita, J. Biochem. 52:367 (1962); Thompson et al., Aust. J. Biol. Science 24: 525 (1971).

Ovalbumin is soluble in electrolyte free water and combines with salts, acids and bases. Denaturation can be induced by heating to 56° C., by vigorous shaking, by electric current and by various chemicals such as acids, ammonium salts, heavy metal salts and alcohols. Such methods produce complete and irreversible denaturation. The isoelectric point of ovalbumin is 4.63. See *Merck Index* ($12^{th}$ Ed. 1996).

In accordance with the compositions and method of the present invention, ovalbumin may be administered in the form of a pharmaceutical composition additionally comprising a pharmaceutically acceptable carrier. One skilled in the art will appreciate that suitable methods of administering the ovalbumin compositions to an animal, such as a mammal, are available and, although more than one method can be used to administer a particular composition, a particular method and dosage can provide a more immediate and more effective reaction than others. Pharmaceutically acceptable carriers are also well known to those skilled in the art. The choice of carrier will be determined, in part, both by the particular composition and by the particular method used to administer the composition. Accordingly, there is a wide variety of suitable formulations of the pharmaceutical compositions of the present invention.

The present invention is preferable in the form of a topical dosage form such as creams, ointments, lotions, gels or powders.

The present invention may be formulated as necessary with additives used commonly in the pharmaceutical sciences, such as surfactants, oils and fats, polyhydric alcohols, lower alcohols, thickening agents, UV absorbents, light scattering agents, preservatives, antioxidants, antibiotics, chelating agents, pH regulators, flavoring agents, pigments and water.

Examples of surfactants include polyoxyethylene (hereinafter abbreviated as POE-branched alkyl ethers such as POE-octyldodecyl alcohol and POE-2-decyltetradecyl alcohol, POE-alkyl ethers such as POE-oleyl alcohol ether and POE-cetyl alcohol ether, sorbitan esters such as sorbitan monooleate, sorbitan monoisostearate and sorbitan monolaurate, POE-sorbitan esters such as POE-sorbitan monooleate, POE-sorbitan monoisostearate and POE-sorbitan monolaurate, fatty acid esters of glycerol such as glyceryl monooleate, glyceryl monostearate and glyceryl monomyristate, POE-fatty acid esters of glycerol such as POE-glyceryl monooleate, POE-glyceryl monostearate and POE-glyceryl monomyristate, POE-dihydrocholesterol ester, POE-hardened castor oil, POE-hardened castor oil fatty acid esters such as POE-hardened castor oil isostearate, POE-alkylaryl ethers such as POE-octylphenol ether, glycerol esters such as glycerol monoisostearate and glycerol monomyristate, POE-glycerol ethers such as POE-glycerol monoisostearate and POE-glycerol monomyristate, polyglycerol fatty acid esters such as diglyceryl monostearate, decaglyceryl decastearate, decaglyceryl decaisostearate and diglyceryl diisostearate and other nonionic surfactants; potassium salts, sodium salts, diethanolamine salts, triethanolamine salts, amino acid salts and other salts of higher fatty acids such as myristic acid, stearic acid, palmitic acid, behenic acid, isostearic acid and oleic acid, the above alkali salts of ether carboxylic acids, salts of N-acylamino acids, N-acylsalconates, higher alkylsulfonates and other anionic surfactants; alkylamine salts, polyamine, aminoalcohol fatty acids, organic silicone resin, alkyl quaternary ammonium salts and other cationic surfactants; and lecithin, betaine derivatives and other amphoteric surfactants.

Examples of oils and fats include vegetable oils and fats such as castor-oil, olive oil, cacao oil, camellia oil, coconut oil, wood wax, jojoba oil, grape seed oil and avocado oil; animal oils and fats such as mink oil and egg yolk oil; waxes such as beeswax, whale wax, lanolin, carnauba wax and candelilla wax; hydrocarbons such as liquid paraffin, squalene, microcrystalline wax, ceresine wax, paraffin wax and vaseline; natural or synthetic fatty acids such as lauric acid, myristic acid, stearic acid, oleic acid, isostearic acid and behenic acid; natural or higher alcohols such as cetanol, stearyl alcohol, hexyldecanol, octyldecanol and lauryl alcohol; and esters such as isopropyl myristate, isopropyl palmitate, octyldodecyl myristate, octyldodecyl oleate and cholesterol oleate.

Examples of polyhydric alcohols include ethylene glycol, polyethylene glycol, propylene glycol, 1,3-butyrene glycol, 1,4-butyrene glycol, dipropylene glycol, glycerol, diglycerol, triglycerol, tetraglycerol and other polyglycerols, glucose, maltose, maltitose, sucrose, fructose, xylitose, sorbitol, maltotriose, threitol and erythritol.

Examples of thickening agents include naturally-occurring high molecular substances such as sodium alginate, xanthene gum, aluminum silicate, quince seed extract, gum tragacanth, starch, collagen and sodium hyaluronate; semi-synthetic high molecular substances such as methyl cellulose, hydroxyethyl cellulose, carboxymethyl cellulose, soluble starch and cationized cellulose; and synthetic high molecular substances such as carboxyvinyl polymer and polyvinyl alcohol.

Examples of UV absorbents include p-aminobenzoic acid, 2-ethoxyethyl p-methoxycinnamate, isopropyl p-methoxycinnamate, butylmethoxybenzoylmethane, glyceryl-mono-2-ethylhexanoyl-di-p-methoxybenzophenone, digalloyl trioleate, 2,2'-dihydroxy-4-methoxybenzophenone, ethyl-4-bishydroxypropylaminobenzoate, 2-ethylhexyl-2-cyano-3, 3'-diphenyl acrylate, ethylhexyl p-methoxycinnamate, 2-ethylhexyl salicylate, glyceryl p-aminobenzoate, homomethyl salicylate, methyl o-aminobenzoate, 2-hydroxy-4-methoxybenzophenone, amyl p-dimethylaminobenzoate, 2-phenylbenzoimidazole-5-sulfonic acid and 2-hydroxy-4-methoxybenzophenone-5-sulfonic acid.

Examples of preservatives include benzoates, salicylates, sorbates, dehydroacetates, p-oxybenzoates, 2,4,4'-trichloro-2'-hydroxydiphenyl ether, 3,4,4'-trichlorocarbanilide, benzalkonium chloride, hinokitiol, resorcinol and ethanol.

Examples of antioxidants include tocopherol, ascorbic acid, butylhydroxyanisole, dibutylhydroxytoluene, nordihydroguaiaretic acid and propyl gallate.

Examples of chelating agents include sodium edetate and sodium citrate.

Examples of antibiotics include penicillin, neomycin, cephalothin, potassium permanganate, selenium sulfide, erythromycin, bacitracin, tethacyclin, chloramphenicol, vancomycin, nitrofurantoin, acrisorcin, chlorodontoin, and flucytosine.

Some of these additives function to enhance the efficacy of the composition by increasing the stability or percutaneous absorbability of the essential components of the present invention.

Also, any dosage form is acceptable, whether in solution, emulsion, powder dispersion, or others. Applicability is wide, including fundamental dosage forms such as lotions, emulsions, creams and gels.

The composition of the present invention is preferrably formulated according to Formula 1:

Phenoxyethanol 1.0% (w/w)
Carbomer 0.5% (w/w)
Ovalbumin 20.0% (w/w)
Triethanolamine 0.3% (w/w)
Suitable vehicle 79.2% (w/w)

The method for processing and pasteurizing hen egg whites is well known in the art and generally involves reverse osmosis, heating, and drying steps resulting in solid egg whites ready for compounding.

In addition to those stated above, suitable vehicles, carriers and adjuvants include water, vaseline, petrolatum, mineral oil, vegetable oil, animal oil, organic and inorganic waxes, polymers such as xanthanes, gelatin, cellulose, collagen, starch, kaolin, carrageenan, gum arabic, synthetic polymers, alcohols, polyols, and the like. The carrier can also include sustained release carrier such as lypizomes, microsponges, microspheres, or microcapsules, aqueous base ointments, water in oil or oil in water emulsions, gels or the like.

The dose administered to an animal, particularly a human, in the context of the present invention should be sufficient to effect a therapeutic response over a reasonable time frame. The dose will be determined by the strength of the particular compositions employed and the condition of the person. The size of the dose and the frequency of application also will be determined by the existence, nature, and extent of any adverse side effects that may accompany the administration of a particular composition.

The composition of the present invention may be employed to treat diabetic ulcers, healing resistant wounds, bed sores, burns, osteomyelitis, trauma wounds, subcutaneous trauma and various forms of dermatitis.

The following examples illustrate the inventive compositions and methods, but should not be regarded as limiting the invention in any manner. Additional studies are in progress as of the filing date of this application.

EXAMPLE 1

In March 1998 a female patient who underwent laminectomy and fusion of T3 and T4 began applying the inventive composition to the surgical wound. This patient experienced no scaring from the surgical wounds and continued to be without scars 10 months post surgery. This patient had a previous history of radical surgery in May 1960 for removal of a right breast tumor. The wound from that surgery healed in approximately one month, but left a large scar. Eighteen months after the May 1960 surgery she had major abdominal surgery, and in 1985 had reconstructive of the right and left breast, but with both surgeries experienced significant scaring. Thus, with the recent surgery, the inventive composition prevented scaring.

EXAMPLE 2

The wound healing characteristics of the inventive composition was demonstrated on Sprague-Dawley rats using a cream according to Formula 1 applied to a wound once daily for five days per week. The percentage of wound acceleration in days and in size was compared to control. The percent of wound acceleration in days was determined to be 5.19, and the percent of acceleration in size was determined to be 22.07.

Note: Percentage wound acceleration in days=(1-TD/CD)×100%, where TD and CD are the days required for 80% wound healing in the treatment and control animals, respectively. Percent wound acceleration in size=(1-TA/CA)×100%, where TA and CA are the areas of the wounds in the treatment in control animals, when 80% wound healing is reached on the former.

EXAMPLE 3

A male patient routinely plagued by muscle and joint soreness and stiffness related to sports activities on the morning following such activities, applied the inventive composition to the affected areas and found that he experienced no joint soreness the mornings following the sports activities.

EXAMPLE 4

Patient number 964885 has been applying the inventive compositions to a diabetic ulcer on the left foot and has experienced a shrinkage of the wound.

EXAMPLE 5

A female applied the inventive composition in a cream form to a third degree burn on her left inner forearm. After daily application of the cream to the affected area, the blister reabsorbed readily, and the area healed within seven days with no residual scar tissue.

EXAMPLE 6

An 88-year-old patient sustained a fall resulting in several facial abrasions and a 1.5 inch laceration over the right eyebrow. With the use of the inventive cream to the affected area, these lacerations healed in about 72 hours leaving no scar tissue.

EXAMPLE 7

A male who has had diabetes for more than 30 years sustained various skin tears and small ulcers on his upper and lower extremities. Daily application of the inventive composition in a cream form has kept the affected areas clean and painfree and healing took place in a relatively short time frame.

EXAMPLE 8

A wound on a dog's hind leg was so extensive that the pad of the paw was almost detached. The inventive composition cream was applied and the wound bandaged. A few days later, the veterinarian noticed remarkable healing in that the wound was clean and dry with a good granulation bed, and there was the beginning of granulation across the wound. The extent of the healing was so great that the dog was able to go home with no bandage on its paw.

Similarly, a filly who had experienced a cut foreleg to the cannon bone was administered the inventive cream and the wound was wrapped. Two days later, upon removal of the bandage and checking of the wound, it had healed nicely across with a base of granulation over the periosteum and showed a good, clean, dry wound bed with moist, supple edges.

EXAMPLE 9

Several patients have used the inventive composition for arthritis, foot calluses, dry skin, back pain, bruises, allergies (including latex allergies), and inflammation. All such patients reported symptomatic relief using the inventive composition.

Analysis of the Composition

The composition of the invention (formula 1) was tested using antibodies directed against bovine and other mammalian derived growth factors. In particular, the antibodies used were targeted toward PDGF, FGF a, FGF b, TGFβ, TGFα, and EGF. The following antibodies were used for detection of the growth factors. Unless noted otherwise the antibodies were purchased from Research Diagnostics Inc., Flanders, N.J.

| Antibodies Catalog Number | Identification | Specificity According to Label |
|---|---|---|
| RDI-PDGFABabg | goat anti-PDGF | Recognizes PDGF-AA, -AB, -BB chains of human, primate, bovine and porcine. |
| RDI-BFGFAabm | mouse anti-FGF Acidic | Recognizes bovine acidic FGF, human acidic FGF and human basic FGF. |
| RDI-BRGFBabm2b. | mouse anti-bovine FGF Basic | Recognizes bovine, rat, mouse and human FGF-b. |
| RDI-TGFBabmx | mouse anti-human TGF-B | Recognizes human, mouse and bovine TGFB1 and B2, also Xenopus TGFB3. |
| RDI-TGFAabmb | mouse anti-human TGF-α | Recognizes mouse, rat and human TGF-α |
| RDI-MSEGFCabg | goat anti mouse EGF C-term | Recognizes mouse and human EGF at carboxy terminus |

Secondary Antibodies

From Jackson Laboratories

Donkey anti-goat IgG (H & L) linked to biotin SP used for EGF and PDGF antibodies.

From Vectastain

Horse anti-mouse (IgG (H & L) linked to biotin used for all other antibodies.

Other Reagents

From Zymed

Streptavidin linked to Horse Radish Peroxidase (HRP) (1:4000)

Protein Determination

Protein concentration was determined by the BCA assay (Pierce) according to manufacture's instructions.

Samples

Samples Provided by B&M Technologies

|  |  |  | Protein conc. By BCA |
|---|---|---|---|
| ppt | MG54-2 | — | 21 mg/ml |
| 1 | MG54-2 | 7-24-97 | 115 mg/ml |
| 2 | MG54-3 | 9-8-97 | 55 mg/ml |

Sample #2 was selected for use in the Western Blot.

Crude Rat Brain Homogenate

For control samples crude rat brain homogenates were generated and run in adjacent lanes to samples of the inventive composition.

Western Blot

Separation of proteins was carried out in modified form from the procedures of Laemmli (Nature 227:680–685 (1970)). Samples and controls were electrophoresed on a 15% SDS-PAGE gel. 40 ug of sample or control was loaded onto each lane. Samples to test for PDGF and TGFB were run under non-reducing conditions as specified by the supplier of the primary antibody. All other samples and controls were run under reducing conditions. The samples were electrophoresed for 45 minutes at 200 V.

The gel was placed on a PVDF membrane and electrophorectically transferred for one hour at 25–30 amps. The membrane was blocked for one hour in PBS containing 5% nonfat dry milk. The primary antibodies were diluted in preparation for incubation with the membrane. Unless otherwise noted the antibodies were diluted in PBS. The concentration of the antibodies used was as follows:

| | |
|---|---|
| Goat anti-Human PDGF-aB | 10 ug/ml |
| Mouse anti-human TGFB | 1 ug/ml in PBS with 1 mg/ml BSA |
| Mouse anti-bovine basic FGF | 1 ug/ml |
| Mouse anti-bovine acidic FGF | 1 ug/ml in PBS with 5 mg/ml BSA |
| Mouse anti-human TGF a | 10 ug/ml |
| Mouse anti-goat EGF | 10 ug/ml |

Lanes were cut from the membrane and incubated overnight at 4° C. with the primary antibody of interest. The membrane strips were washed for one hour in PBS-tween (0.05% Tween 20) and incubated for two hours with the secondary antibody of choice diluted in PBS. For lanes incubated with goat derived primary antibodies, biotin linked donkey anti-goat IgG at 1:10,000 dilution was used as secondary antibody. For lanes incubated with mouse derived primary antibody, biotin linked horse anti-mouse IgG at 7.5 ug/ml diluted in PBS (1:200) with 1% normal horse serum was used as secondary antibody. The membrane strips were washed for one hour in PBS and incubated with either streptavidin-HRP for one hour (Zymed 1:4000, for donkey anti-goat IgG stained strips) or Vectastain AB reagent (Avidin DH linked to Biotinylated peroxidase) for 30 minutes (for horse anti-mouse IgG stained strips). The strips were washed for 30 minutes in PBS and developed using diaminobenzadine tetrahydrochloride (DAB). The membrane strips were washed for 10 minutes in PBS and air dried.

Results

A preliminary Western run to test the response of the antibodies was run without controls. Antibodies to PDGF and TGF β showed little activity against the inventive composition (lane 6 PDGF, 7 TGF B). Antibodies to EGF, TGF α, FGF α, FGF β, (lanes 1–4, respectively) had identical binding to the invention with bands at 70 kDa, 32–34 kDa and 15–17 kDa.

While the specific invention has been described with an emphasis upon preferred embodiments, it will be obvious to those of ordinary skill in the art that variations in the preferred methods of the present invention may be used and that it is intended that the invention may be practiced otherwise than as specifically described herein. Accordingly, this invention includes all modifications encompassed within the spirit and scope of the invention as defined by the following claims.

I claim:

1. A composition for accelerating wound healing in a subject in need thereof, comprising: about 5.0% to 20% by weight crude ovalbumin containing a growth factor selected from the group consisting of epidermal growth factor, transforming growth factor alpha, fibroblast growth factor alpha, and fibroblast growth factor basic; about 1.0% by weight phenoxyethanol, about 0.5% by weight carbomer; and about 0.3% by weight triethanolamine.

2. The composition according to claim 1, in the form of a gel.

3. The composition according to claim 1, in the form of a cream.

4. The composition according to claim 1, in the form of a lotion.

5. The composition according to claim 1, in the form of an ointment.

6. A method for stimulating wound healing in a subject in need thereof, comprising: applying a pharmacologically effective amount of a composition to the wound of the subject, the composition comprising about 5.0% to 20% by weight crude ovalbumin containing a growth factor selected from the group consisting of epidermal growth factor, transforming growth factor alpha, fibroblast growth factor alpha, and fibroblast growth factor basic; about 1.0% by weight phenoxyethanol, about 0.5% by weight carbomer; and about 0.3% by weight triethanolamine; wherein the amount of the composition applied to the skin increases local wound healing activity of the subject's skin.

7. A method for stimulating hair growth in a subject in need thereof, comprising: applying a pharmacologically effective amount of a composition to the skin of the subject, the composition comprising about 5.0% to 20% by weight crude ovalbumin containing a growth factor selected from the group consisting of epidermal growth factor, transforming growth factor alpha, fibroblast growth factor alpha, and fibroblast growth factor basic; about 1.0% by weight phenoxyethanol, about 0.5% by weight carbomer; and about 0.3% by weight triethanolamine; wherein the composition stimulates hair follicle growth on the skin of the subject.

8. The composition of claim 1, wherein the growth factor is epidermal growth factor.

9. The composition of claim 1, wherein the growth factor is transforming growth factor alpha.

10. The composition of claim 1, wherein the growth factor is fibroblast growth factor alpha.

11. The composition of claim 1, wherein the growth factor is fibroblast growth factor basic.

12. The composition of claim 1, wherein the wound is selected from the group consisting of an ulcer, burn, osteomyelitits, trauma wound, subcutaneous trauma wound, dermatitis, sports injury, muscle soreness, joint soreness, muscle stiffness, joint stiffness, laceration, scarring, surgical wound, arthritis, foot calluses, dry skin, back pain, bruise, and inflammation.

13. The composition of claim 1, wherein the composition is in a form of a topical composition.

14. The composition of claim 1, wherein the composition is in a form of a solution, emulsion, powder, or dispersion.

15. The composition of claim 1, wherein the crude ovalbumin is from hen egg white.

16. The composition of claim 1, wherein the composition further comprises a surfactant, oil, fat, alcohol, thickening agent, UV absorbent, light scattering agent, preservative, antioxidant, chelating agent, or antibiotic.

17. The method of claim 6, wherein the composition is in a form of a topical composition.

18. The method of claim 6, wherein the composition is in a form of a gel, cream, lotion, ointment, or powder.

19. The method of claim 7, wherein the composition is in a form of a topical composition.

20. The method of claim 7, wherein the composition is in a form of a gel, cream, lotion, ointment, or powder.

* * * * *